United States Patent
Castelli

(10) Patent No.: US 6,530,893 B1
(45) Date of Patent: Mar. 11, 2003

(54) CARPAL TUNNEL SYNDROME TRACTION SYSTEM

(76) Inventor: Judith M. Castelli, 211 Buckskill Rd., East Hampton, NY (US) 11937

(*) Notice: Subject to any disclaimer, the term of this patent is extended or adjusted under 35 U.S.C. 154(b) by 0 days.

(21) Appl. No.: 09/824,383

(22) Filed: Apr. 2, 2001

Related U.S. Application Data

(60) Provisional application No. 60/199,150, filed on Apr. 25, 2000.

(51) Int. Cl.[7] .................................................. A61F 5/00
(52) U.S. Cl. .......................................... 602/32; 602/36
(58) Field of Search ............................ 482/125, 44, 79, 482/124; 602/32, 35, 36, 38, 39, 40

(56) References Cited

U.S. PATENT DOCUMENTS

| | | | | |
|---|---|---|---|---|
| 4,869,499 A | * | 9/1989 | Schiraldo | 272/137 |
| 5,558,609 A | * | 9/1996 | Olschansky | 482/122 |
| 5,613,923 A | * | 3/1997 | Anliker | 482/48 |
| 5,632,726 A | | 5/1997 | Repice et al. | |
| 5,702,355 A | | 12/1997 | Repice et al. | |
| 5,707,345 A | | 1/1998 | Fulk | |
| 5,967,947 A | | 10/1999 | Glover | |

* cited by examiner

Primary Examiner—Michael A. Brown
(74) Attorney, Agent, or Firm—Collard & Roe, P.C.

(57) ABSTRACT

This invention encompasses, methods, devices and system for prevention and relief of carpal tunnel syndrome in the wrist through the use of traction. The device contains a wrist member, an anchor member connected at one end each of an interconnecting adjustable interface member. The apparatus for applying extremity traction contains a tensioning cable and a retaining device attached to the tensioning cable as well as an anchor member.

13 Claims, 11 Drawing Sheets

CARPAL TUNNEL SYNDROME TRACTION SYSTEM

CROSS-REFERENCE TO RELATED APPLICATIONS

This application claims the benefit of the filing date of abandoned Provisional Application Ser. No. 60/199,150 filed Apr. 25, 2000.

BACKGROUND OF THE INVENTION

1. Field of the Invention

This invention relates to prevention and relief of carpal tunnel syndrome through the use of traction. More particularly, it relates to relieving carpal tunnel syndrome and conditions of the lower extremities. One end of the device anchors to a fixed anchor, such as a door knob, and the other end is attachable to the wrist.

2. The Prior Art

Traction can be an effective non-surgical treatment of Carpal Tunnel Syndrome and other associated conditions such as pain, numbness, tingling in the fingers, swelling and pain in the elbows, forearms, wrists, hands and fingers. Such treatment can also be effective for the lower extremity including of disorders of the foot, ankle, knee, etc., and for treatment of the neck.

The effectiveness of applying traction in the treatment of Carpal Tunnel Syndrome is based on its ability to re-stretch the muscles, tendons, ligaments, nerves and blood vessels in the forearm and wrist areas which relieves pressure on the median nerve and which in turn allows for reduction of the inflammation, pain and weakness which is typical of Carpal Tunnel Syndrome (C.T.S.).

After unsuccessful attempts to reverse the progress of the disorder by eliminating the repetitive work which often causes Carpal Tunnel Syndrome, taking anti-inflammatory medications, or wearing splints on the affected wrist(s), the treatment of choice for C.T.S. has been surgery, which makes room for and relieves pressure on the median nerve within the carpal tunnel canal.

Previous traction devices are cumbersome, involve weights, ropes and pulleys, locking cams, surgical attachment to body, and were designed for other applications such as traction during surgery, post-surgical traction, or traction for broken bones. These traction devices were meant to be in place for long periods of time while the body healed from injury or surgery.

An example of one newer, non-surgical, non-invasive treatment option for Carpal Tunnel Syndrome is U.S. Pat. No. 5,707,345. This large, motorized, expensive device relies upon air pressure to create traction. This machine is often found in today's well-equipped physical therapy/rehabilitation center. The patient is seated next to the machine by the therapist, who straps the forearm onto the stationary deck, and a wrist harness is wrapped around the patient's wrist. The harness is attached to the drive member that moves along a track using air pressure, pulling the wrist harness away from the patient's elbow for a pre-set distance.

Traction is held for a number of seconds, and the machine releases the traction. The process repeats for approximately 10 minutes. The recommended treatment is often three times a week for an average of three months. Needless to say, this is an expensive and time-consuming treatment plan involving many visits to the physical therapist.

The disadvantage of the prior art for curing and relieving carpal tunnel syndrome of the wrist is that they are cumbersome, involve weights, ropes and pulleys, locking cams, surgical attachment to body.

Furthermore, the prior art devices are not portable, aesthetic, affordable, quick, simple, convenient or secure enough.

All the problems with prior art traction devices can be categorized into the following:

Not suitable for Do-It-Yourself patient; Not elegant nor aesthetic; Emphasizes cure rather than prevention; Neither portable, nor affordable; Not integrated into a slim aesthetic portable design; Not cost effective due to excessive parts and or manufacturing steps; Do not harmonize with the environment; Not anchor-able to either vertical or horizontal anchor; Cumbersome; Involve weights; Involve ropes; Involve pulleys; Involve locking cams; and involve surgical attachment to body; Not self-contained, and not controllable by the user.

Examples of related prior art can be seen in U.S. Pat. No. 5,967,947 to James Glover on Oct. 19, 1999 for "Isometric Wrist Exercise Device". U.S. Pat. No. 5,702,355 to Ronald Repice on Dec. 30, 1997 for "Portable Adjustable Traction Appliance to Treat Carpal Tunnel Syndrome and Other Problems of the Wrist. U.S. Pat. No. 5,632,726 to Ronald Repice on May 27, 1997 for "Device for Use on a Traction Machine to Treat Carpal Tunnel Syndrome and Other Problems of the Wrist".

However, these references do not disclose the embodiment of the present invention being a simple, elegant, quick, convenient, affordable and secure solution.

SUMMARY OF THE INVENTION

An object of the present invention is to provide a method, device and system for prevention and relief of carpal tunnel syndrome for the wrist or the neck or the like organ.

Another object of this invention is to provide an aesthetic and elegant design that integrates harmoniously with any environment.

Another object of this invention is that its use is quick, simple, convenient and easy.

Another object of this invention is that it be suitable for all types of users in all types of conditions.

Another object of this invention is that its design is simple and even elegant.

Another object of this invention is that its use is intuitive which requires no further training.

Another object of this invention is that it be capable of multiple uses.

Another object of this invention is that it use little or no additional energy.

Another object of this invention is that one size fit all types and sizes of bottles.

Another object of this invention is that the invention use modular standard components easily interfaceable to each other.

Another object of this invention is that it be reliable such that it practically never fails and requires little or no maintenance.

Another object of this invention is that it be made from biodegrade materials to the extent practical.

Another object of this invention is that it be environmentally safe.

Another object of this invention is that it be physically safe in normal environment as well as accidental situations.

Another object of this invention is that it be long lasting made from durable material.

Another object of this invention is that it meet all federal, state, local and other private standards guidelines, regulations and recommendations with respect to safety, environment, energy consumption.

Another object of this invention is that it be suitable for both professional therapist as well as Do-It-Yourself therapist.

Another object of this invention is that it be suitable for gift giving.

Another object of this invention is that it be suitable for promotional give aways complete with message of the sponsor such as a casino or church.

Another object of the invention is to provide an inexpensive, easily available, simple device to apply traction to the extremity or neck and process for doing same.

Another object of the invention is to provide a traction device that is lightweight, portable, inexpensive to manufacture, and easy to use.

Another object of the invention is to provide a self-treatment traction device that requires no assistance by medical or physical therapy personnel.

Another object of this invention is to obviate the necessity of expensive equipment, weights, pulleys, motorized equipment, or surgical attachment to the user.

Another object of this invention is to provide a self-treatment traction device for the treatment of Carpal Tunnel Syndrome.

Other objects of this invention reside in its simplicity, elegance of design, ease of manufacture, service and use and even aesthetics as will become apparent from the following brief description of the drawings and the detailed description of the concept embodiment.

Another object of this invention is that it be self-contained.

Another object of this invention is that it operate without external anchoring or other external instrumentality by a loop around a patient's own body acting as an anchor.

The present invention accomplishes these and other objects by providing a Carpal Tunnel Syndrome prevention and relief traction system comprising a wrist or neck member attachable to a wrist of user. An anchor member is attached to a fixed point and an interface interconnecting adjustable member is connected between the wrist member and the anchor member.

In accordance with a preferred embodiment of the present invention, the apparatus for applying extremity traction comprises a tensioning cable and a retaining device attached to the tensioning cable as well as an anchor member.

In accordance with another embodiment of the present invention, a method of using an apparatus as above comprises the steps of affixing the tensioning cable to a fixed object, moving the extremity away from the fixed object causing tension at the extremity, moving the extremity toward the fixed object releasing tension at the extremity, and repeating moving away from and moving toward the fixed object one or more times. The fixed object may be a the user's foot, a doorknob, a hook on a wall or the like.

In another embodiment of the present invention, a method of using an apparatus as above comprises the steps of causing tension in the tensioning cable causing traction at the extremity, including the neck, removing tension in the tension cable releasing tension at the extremity or neck, and repeating causing tension and releasing tension in the tension cable one or more times. The tension may be caused by moving the retaining device away from a fixed object, or by moving an object attached to the tensioning cable, such as a foot, away from the retaining device.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 9:
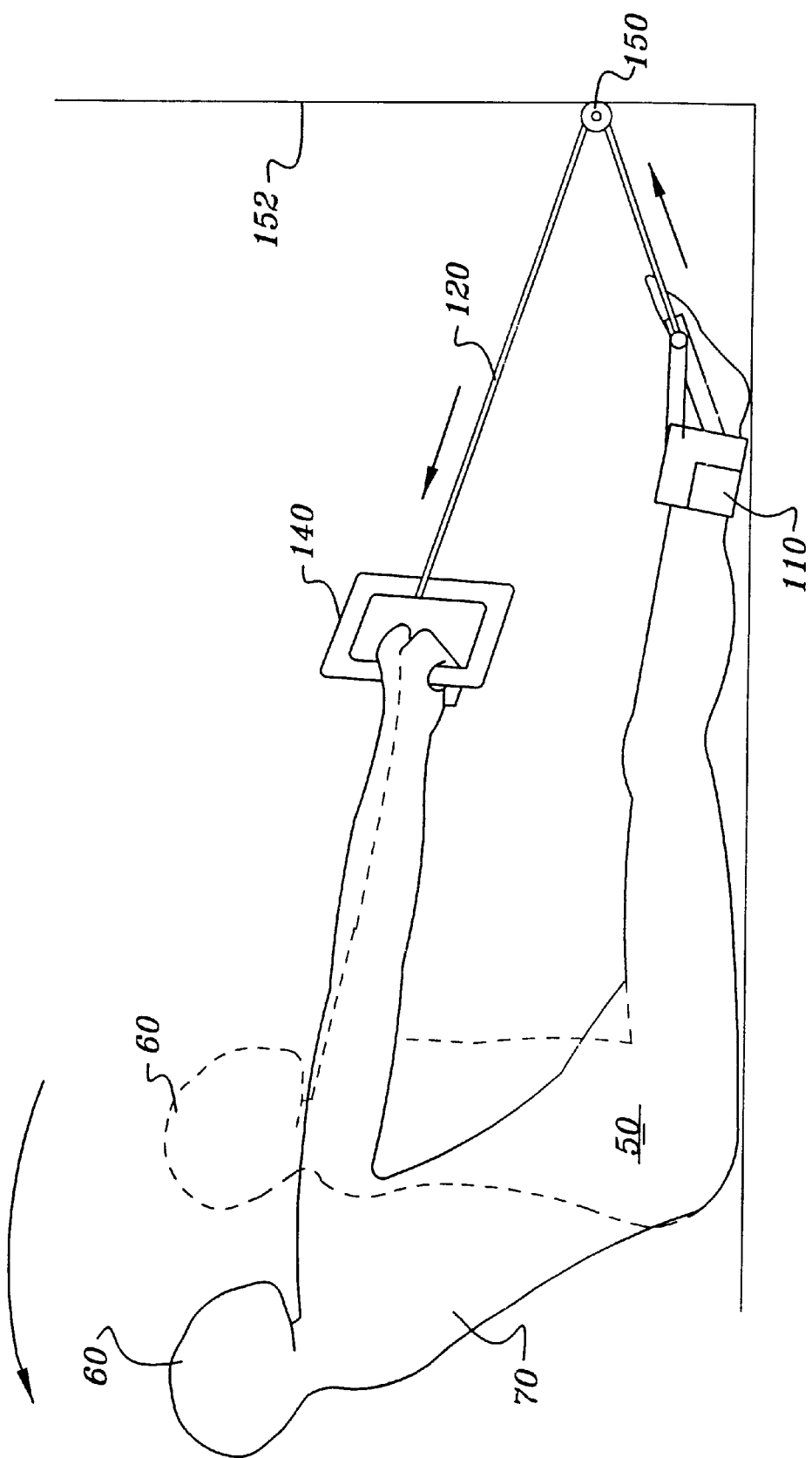
FIG. 9 shows an illustration of a yet another method of the present invention where the tensioning cable passes through a receptacle on a stationary object and the user pulls the tensioning cable away from the stationary object causing tension on the extremity retaining device thereby causing traction to the lower extremity.
Figure 10:
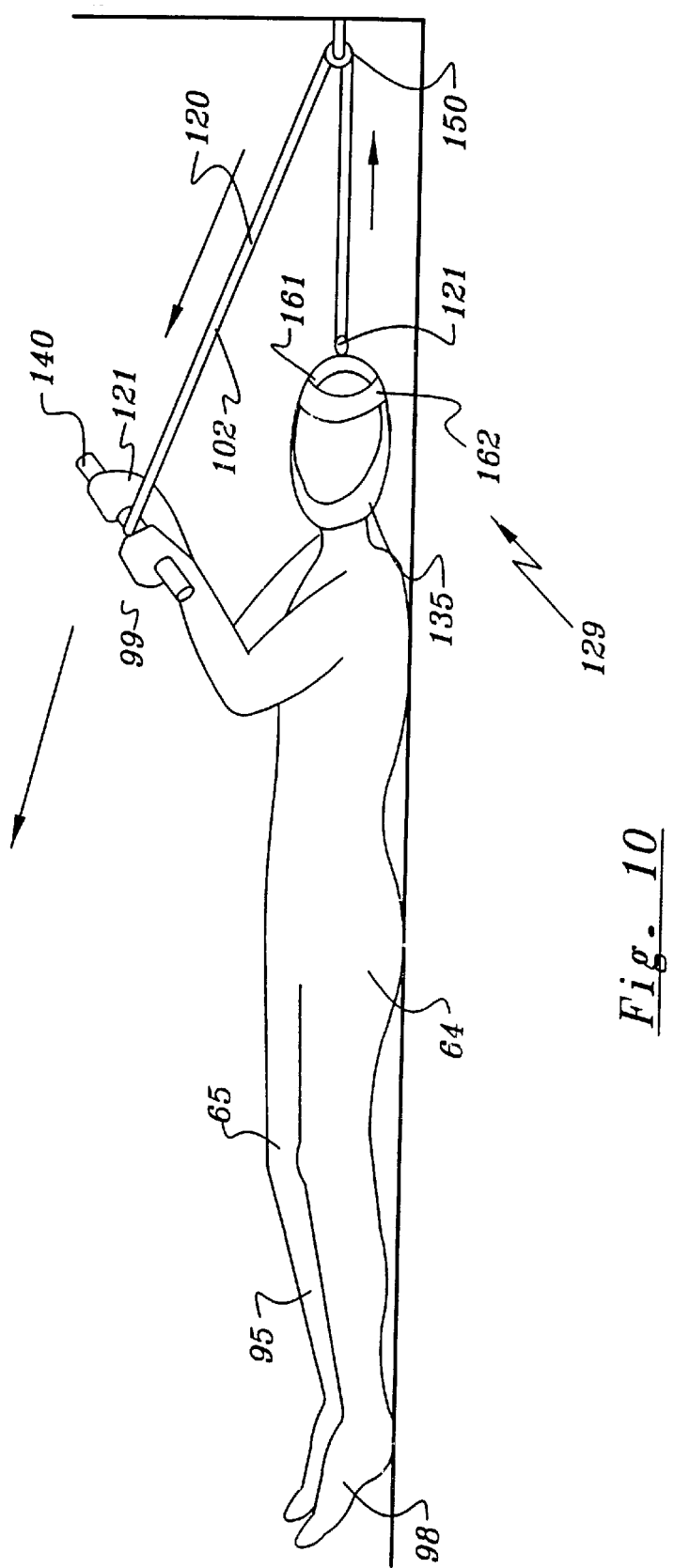
FIG. 10 shows an illustration of still another method of the present invention where the whereby the tensioning cable passes through a receptacle on a stationary object and the user pulls the tensioning cable away from the stationary object causing tension on the head retaining device thereby causing traction to the neck.

The invention will be described as applied to applying tension to an upper extremity, but is also applicable to causing tension in a lower extremity as illustrated in FIG. 9 and to the neck as illustrated in FIG. 10.

Figure 1:
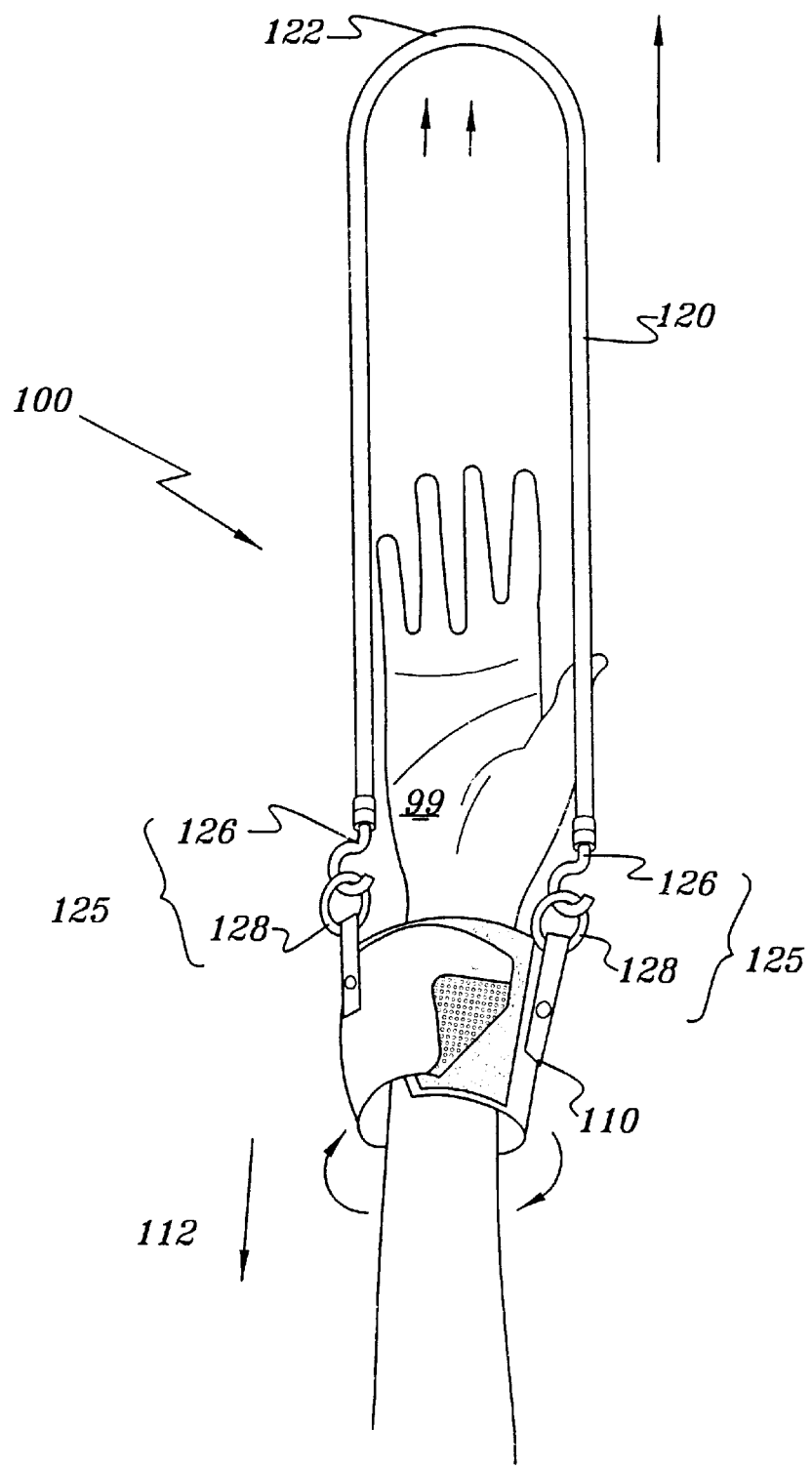
FIG. 1 shows a perspective view of an extremity traction apparatus in accordance with a preferred embodiment of the present invention.

Referring now in detail to the drawings and, in particular, FIG. 1, tensioning cable 120 is shown and is to attach a wrist retaining device 112. Cable 120 and retaining device 112 are connected in such a manner as to form a loop 122 in the tensioning cable 120. In the practice of the invention, loop 122 formed in the tensioning cable 120 is used to apply and release traction to the upper extremity, as described below.

Figure 2:
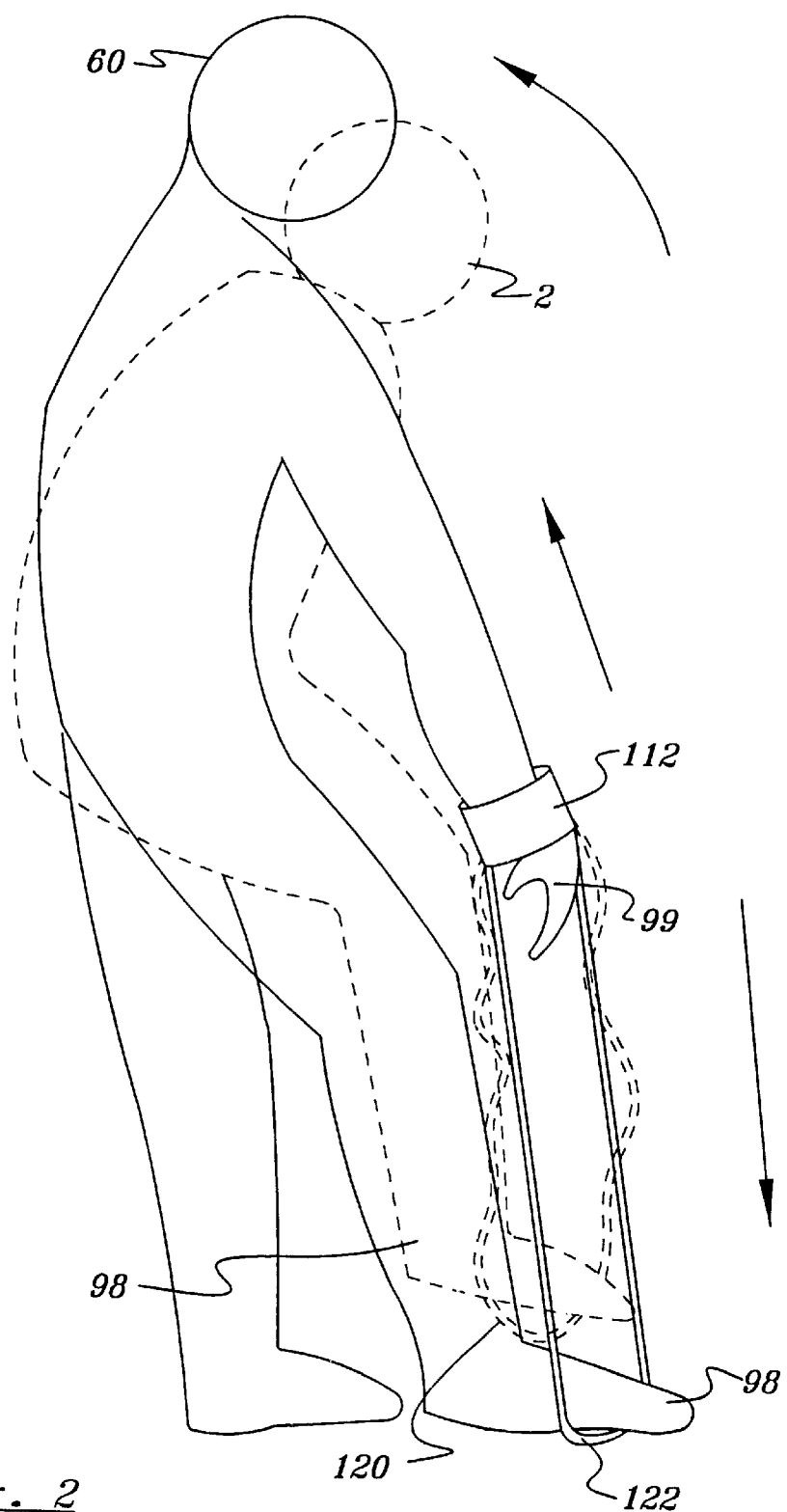
FIG. 2 shows an illustration of the preferred method of the present invention where the user moves the extremity retaining device away from a stationary object, which is the user's foot, to cause traction.

Following a preferred procedure as illustrated in FIG. 2, the user wraps the wrist retaining device 112, which can be a padded 114 collar with hook and loop fasteners 125 around the wrist just below the hand 22. Retaining device 21 may also be a glove-like device illustrated in FIGS. 7 and 8. Tensioning cable 120 is attached by the user to the wrist retaining device as previously described, and the loop 122 in tensioning cable 120 is connected to a stationary object which may be the user's foot 98. Further, in the preferred procedure, the user lifts their upper body 90 to a more erect position thereby applying traction to the upper extremity.

Following the preferred procedure the user maintains traction for the desired length of time and the user releases tension on the cable by lowering the upper body. The process is repeated a number of times during a self-treatment session thereby gradually stretching the muscles, ligaments, tendons, nerves and blood vessels of the upper extremity of the user.

As a consequence of the intermittent traction, the stretching of the muscles, ligaments, tendons, nerves and blood vessels of the wrist and forearm relieves pressure on the median nerve which in turn alleviates the symptoms of Carpal Tunnel Syndrome.

To further explain a preferred procedure using the apparatus as shown in FIG. 1, the user wraps the padded 114 retaining device 112 around the wrist 97 just below the hand 99. In the preferred embodiment, retaining device 112 is a strip of padded leather or similar material, affixed to the wrist 97 by a hook and loop fastener system 125 as is well shown. Retaining device 112 is wrapped loosely around the wrist 97, yet it must be wrapped tightly enough so that it cannot slip over the hand 99 during use.

Once the retaining device 110, 112 is in place, the tensioning cable 120 can easily be attached to the retaining device 110 in such a way as to form a loop 122 as depicted in FIG. 1. In the preferred embodiment, tensioning cable 120 is an elastic "bungie" cord 11 with hook fasteners 125 at each. Further, the two hooks 126 on the ends of the tensioning cable 120 are fastened to retaining device by means of two metal rings 128 which may be on adjustable straps 130 thus forming a loop 122 in tensioning cable 120. Other means of attachment may include leather straps with snap fasteners, button and buttonhole, grommets, clamping devices, self-locking closures as in key chains, or dog leashes, and other familiar means.

FIG. 2 illustrates a preferred method for the application of traction to the upper extremity from a standing position.

The user 50, bending forward from the waist, puts the foot 98 into the loop of the tensioning cable 120 and stands on the cable 120. In keeping with the invention, the user attempts to come to a fully erect posture 60 pulling upward on the tensioning cable 120 thereby applying traction to the upper extremity. Lowering the upper body to its original position releases the traction whereupon the process is repeated causing intermittent traction.

The process of traction, holding traction, and releasing traction, is repeated for a specified number of repetitions or for a desired length of time. Thus, in the present embodiment it is seen that this is a process for self-treatment that the user implements and controls.

Referring again to FIG. 1 other methods of attaching loop 122 to a stationary object can be imagined. In an alternate embodiment, cable 120 may be of a single strand of material not looped, but having a handle member 140 at the distal end of cable 120 from retaining device 112. The handle 140 may itself be a loop that the user affixes to the stationary object, or pulls away from the retaining device. Further, the loop or handle may be metal, plastic, wood, leather or similar sturdy material.

The loop or handle may also be adjustable or self-locking to insure that it engages securely with the stationary object which may be a metal ring, hook, or eyelet or similar object affixed to a stationary object such as a wall, door, molding, furniture or the like.

It is noted that the tensioning cable can be non-permanently attached to the retaining device to assure the user ease in affixing the retaining device to the user's extremity or neck.

The application of traction to the upper extremity may be accomplished in various ways as decided by the user without departing from my invention as illustrated in FIGS. 3, 4, 6, 9, and 10.

Figure 3:
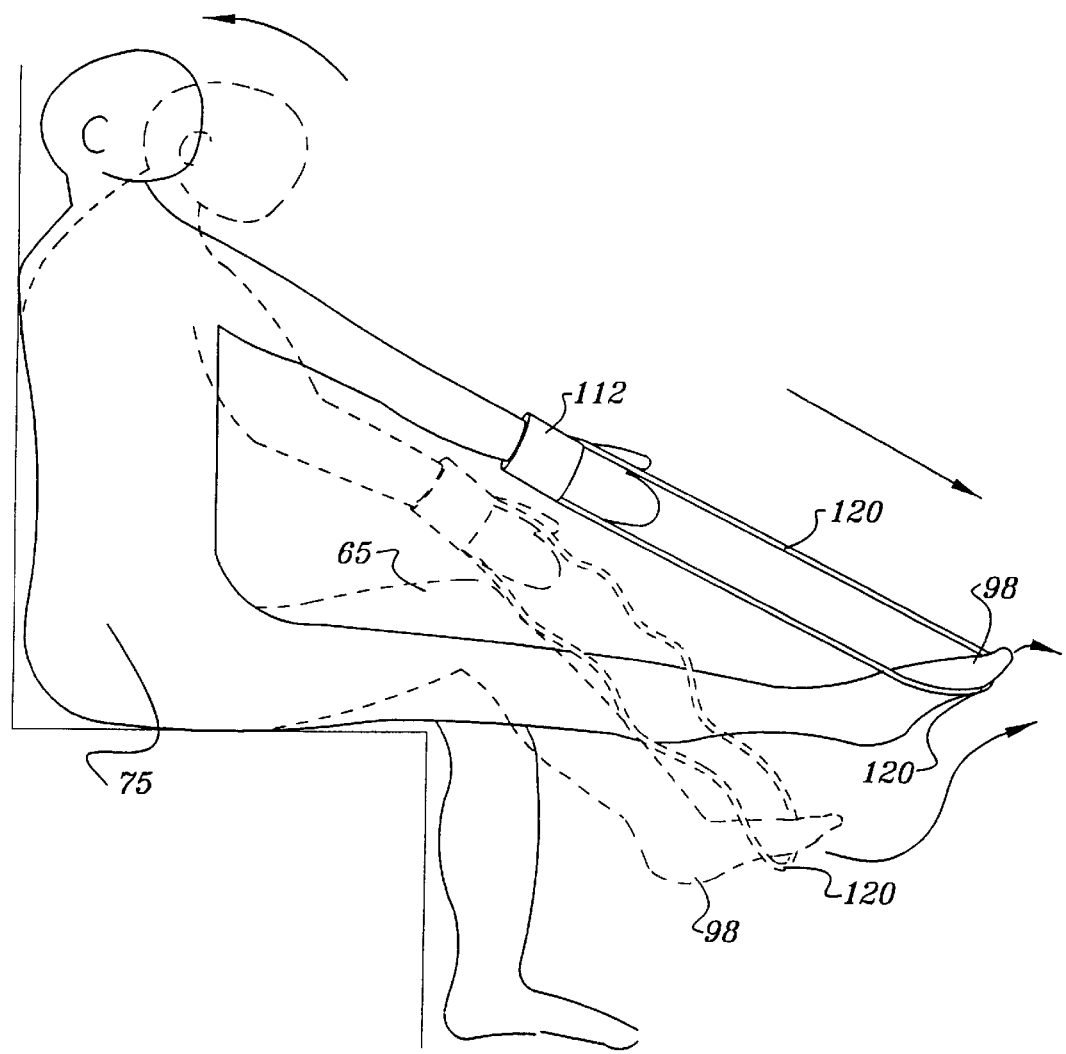
FIG. 3 shows an illustration of another method of the present invention where the user moves the distal portion of the tensioning cable away from the extremity retaining device by straightening the leg while in a seated position to cause traction.

FIG. 3 illustrates a process for application of traction from a seated position 62. This method is useful for example while in the office, or on a road trip. With all elements of the device in place, the user in a seated position 62 with the knee 65 flexed, inserts foot 98 into the loop 122 of the tensioning cable 120. Foot 98 is thrust forward, knee 65 is straightened, and cable 120 is pulled in a direction away from the retaining device 112. Traction is thereby placed on extremity.

In the further practice of the invention, the user 50 bends knee 65 again, returning the body to the original position. Thus, traction is released whereupon the process is repeated.

Figure 4:
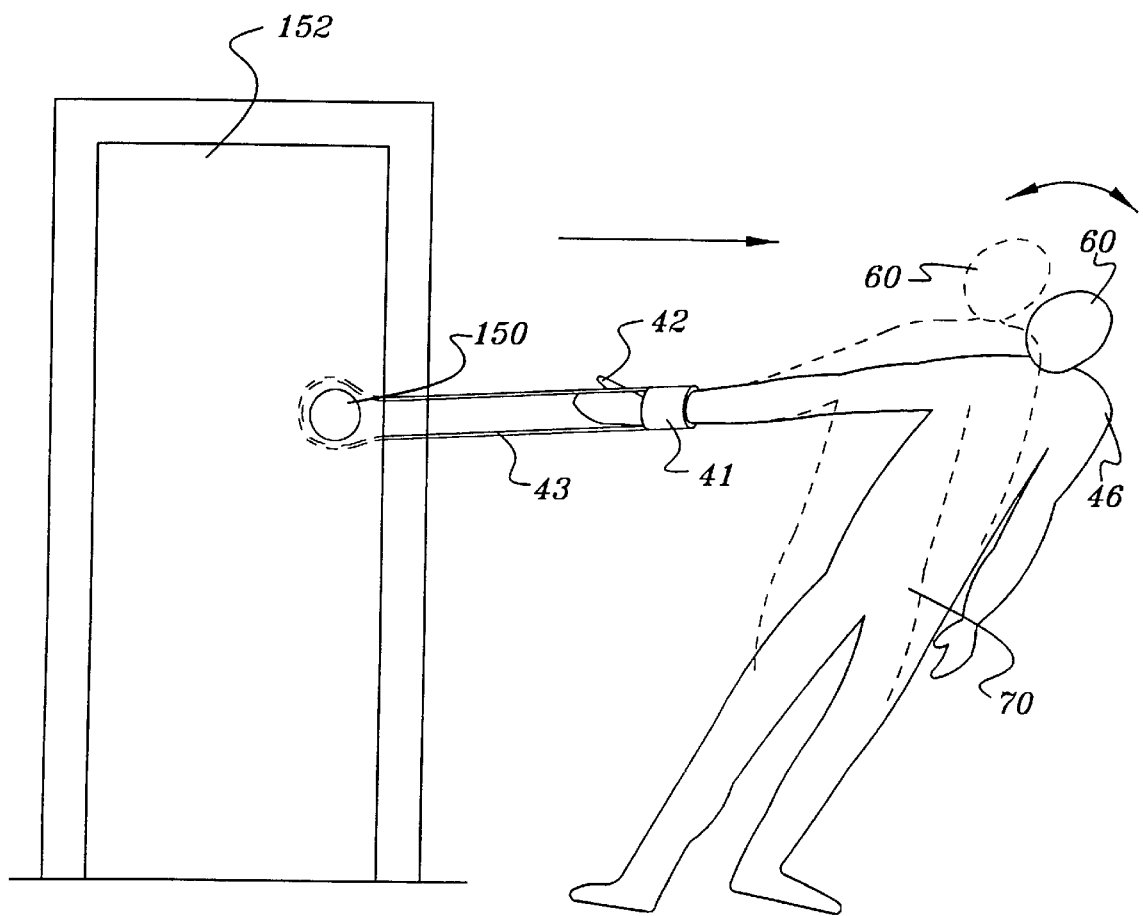
FIG. 4 shows an illustration of another method of the present invention where the user moves the extremity retaining device away from a stationary object which can be a doorknob to cause traction.

FIG. 4 illustrates another process for application of traction from a standing position. User 50, in an upright position 60, wraps wrist restraining device 112 which can be a padded collar 114 with hook and loop fasteners 125 around the wrist 97 just below the hand 99.

Figure 7:
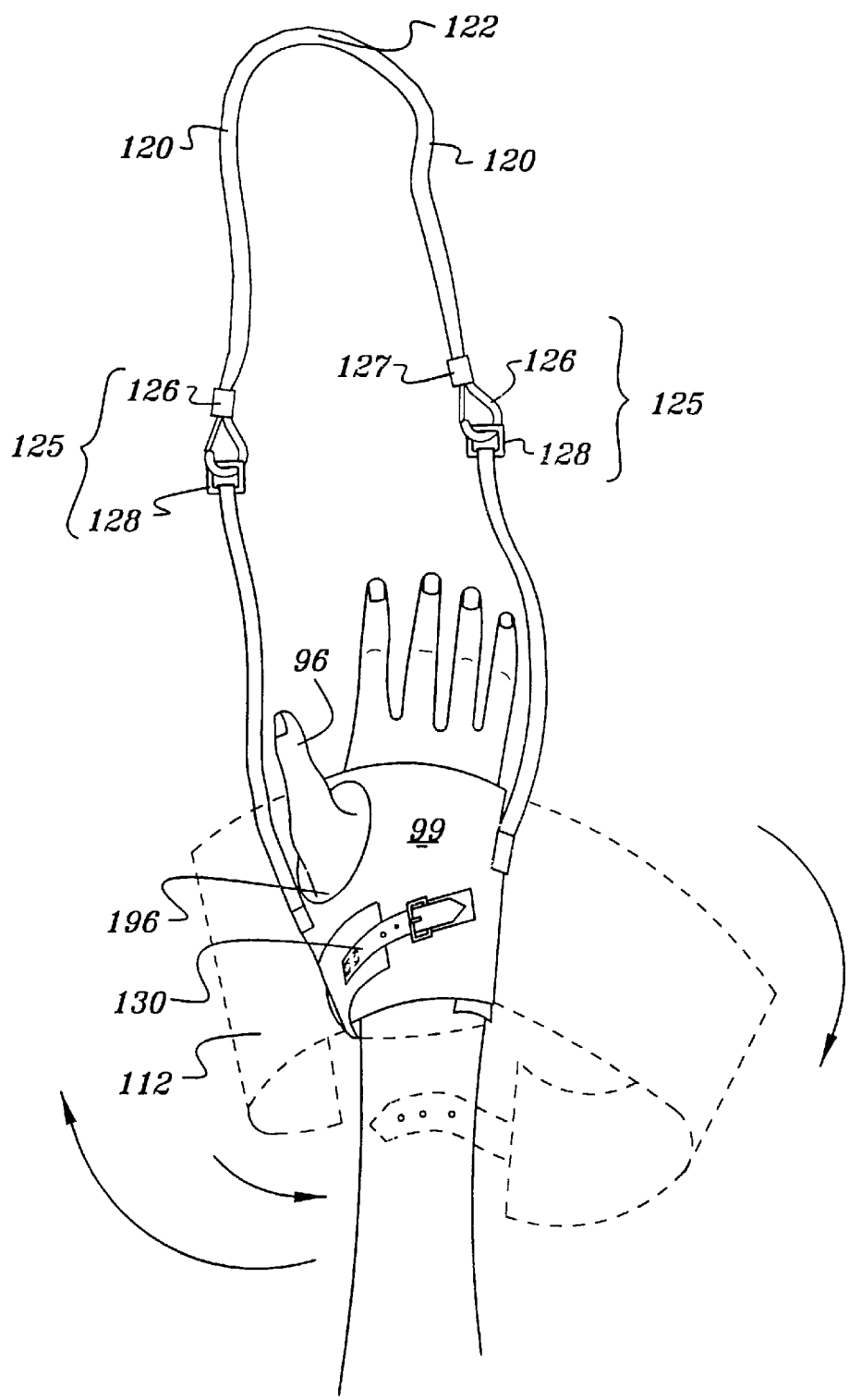
FIG. 7 shows a perspective view of a glove-like hand retaining device attached to a tensioning cable.
Figure 8:
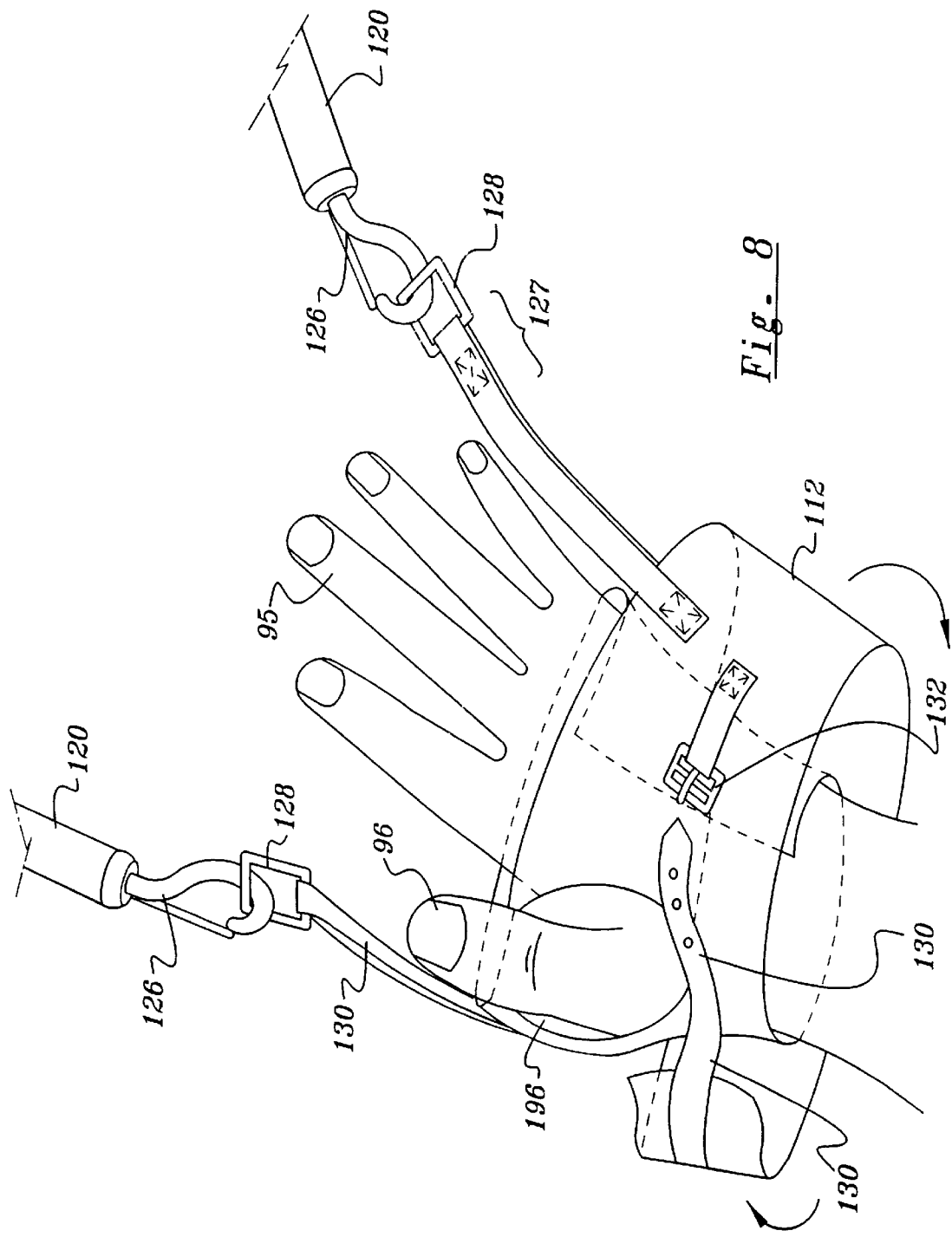
FIG. 8 shows a detail perspective view of the glove-like hand retaining device affixed to the tensioning cable by self-locking hooks.

Retaining device 112 may also be a glove-like device illustrated in FIGS. 7 and 8. Tensioning cable 120 is attached by the user to the wrist restraining device 112 as previously described, and the loop 122 in tensioning cable 120 is connected to a stationary object which may be a door knob 150. Further, in the preferred procedure, the user 50 leans his or her body 90 away from the doorknob 150 thereby applying traction to the upper extremity.

Figure 5:
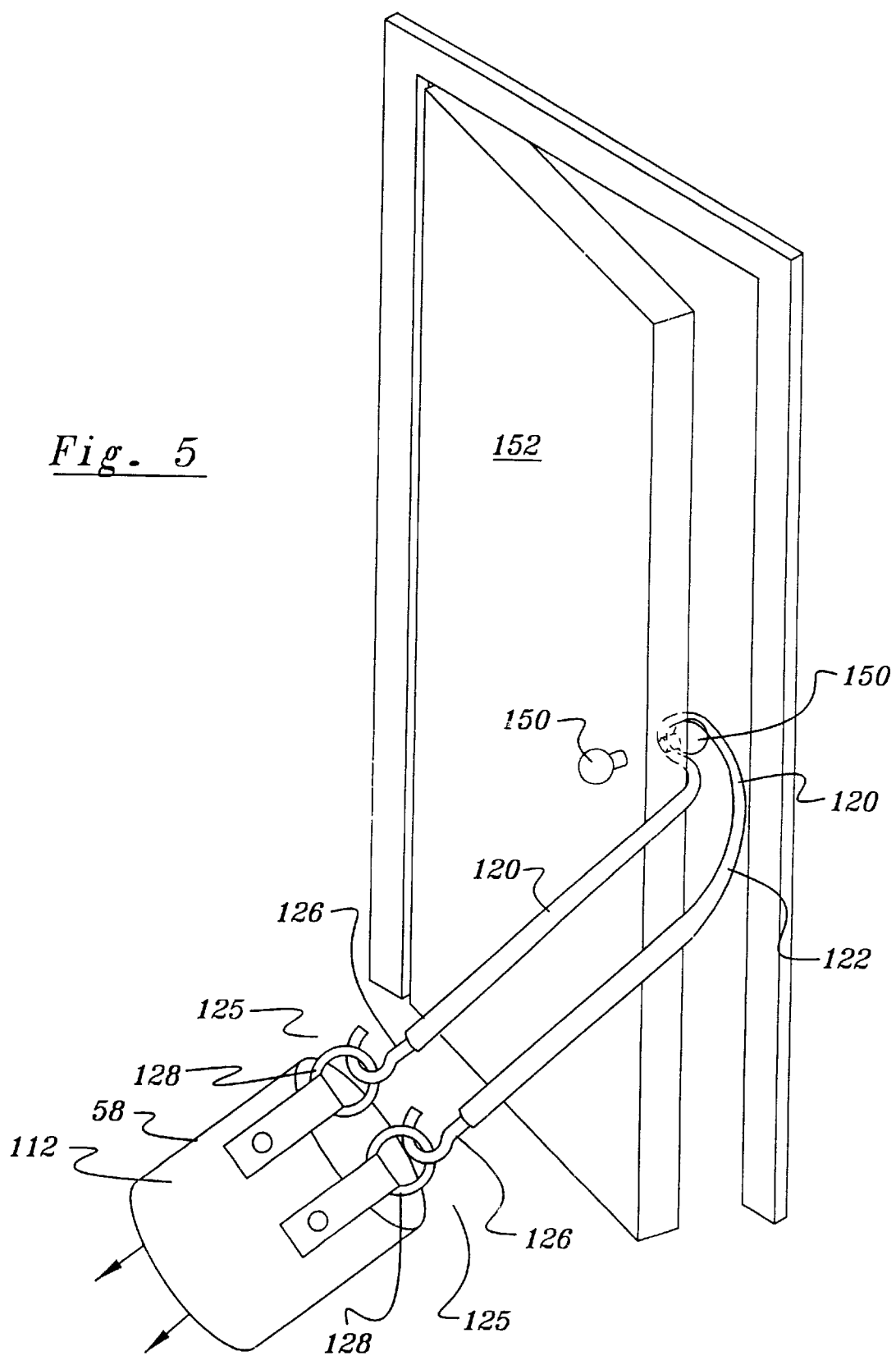
FIG. 5 shows a perspective view of the invention with the tensioning cable affixed to a stationary doorknob.

Referring in detail to FIG. 5, the loop created in the tensioning cable 120 hooks over the far doorknob 150, i.e., the knob that is not in the room with the user, of a door 152 that closes toward the user 50, who user closes the door 152 on the tensioning cable 120 thus assuring that both the cable 120 and door 152 are secure.

Figure 6:
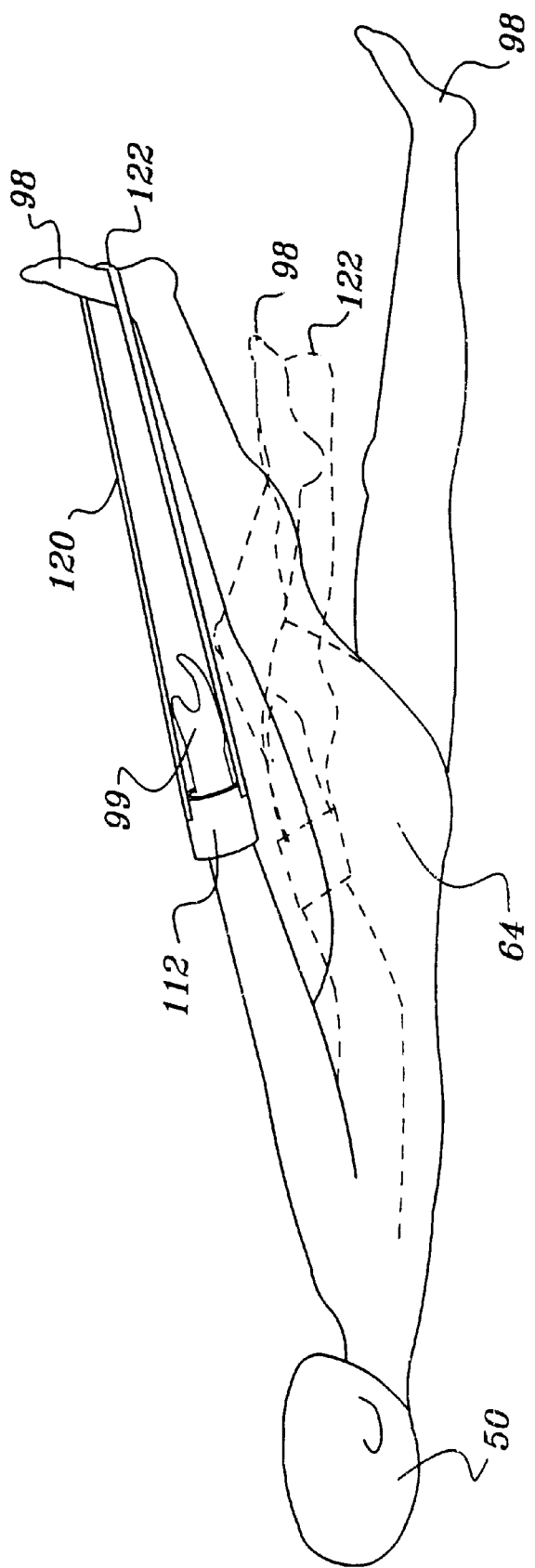
FIG. 6 shows an illustration of yet another method of the present invention where the user, while lying on their back, moves the distal portion of the tensioning cable away from the extremity retaining device by straightening the leg to cause traction on the upper extremity.

FIG. 6 illustrates the application of traction to the upper extremity when the user 50 is in reclining position 70, on his or her back with knee bent 166. The user 50 slips the loop 122 of the tensioning cable 120 over the foot 98, and straightens the leg 95, extending the foot 98 forward and away from the retaining device 110 thereby applying traction to the upper extremity. Returning the leg 95 to the original position with knee bent 166, releases the traction whereupon the process is repeated.

In accordance with the present invention, FIG. 7 illustrates a glove-like hand retaining device 115, comprising an encompassing leather band 130 and further comprising a thumb receptacle 196 into which the user's thumb 96 is inserted. The hand retaining device 112 may also be fabricated from cotton, nylon or other comfortable and sturdy natural or man-made material. A variety of devices and other restraining devices are well known in the art and may be employed to restrain the extremity.

FIG. 8 further illustrates that the encompassing band 130 wrapped around the girth of the hand 99 and overlaps to form a cylinder 129. Referring again to FIG. 7, the device further comprises metal loops 128 or other means to attach to the tensioning cable 120 for applying traction to the upper extremity. It should be noted that the attaching mechanism 128 should be positioned on either side of the user's 50 hand 99 to allow traction to be applied evenly.

The hand 99 retaining device 112 further comprises a single or multiple adjustable strap 130 with buckle 132 to affix the device to the user's 50 hand 99.

FIG. 8 is a detailed view of a glove-like hand retaining device 115. In accordance with the present invention, FIG. 8 further illustrates a hand retaining device comprising an encompassing band 130 which can be a strip leather, neoprene, nylon covered foam, woven cotton, or like materials, and further comprising a thumb receptacle 196 into which the user's thumb 96 is inserted.

Further, the band 130 is wrapped around the girth of the hand 99 and overlaps to form a cylinder 129 and further comprising straps with metal loops 128 or other means to attach to self-locking hooks or similar means for applying traction to the upper extremity. The hand retaining device 112 further comprises a single or multiple adjustable strap(s) 130 with buckle 132 to secure the hand 99 retaining device 112 to the user 50.

FIGS. 7 and 8 illustrate the hand retaining device 112 for use on the right hand and that the device for the left hand would be manufactured in a similar manner with but with a reverse configuration of thumb 96, straps with metal loops 72 and 73, and adjustable strap/s 130 with buckle 132. A reversible or universal device may be employed for use with either hand, and are well known in the field.

In accordance with a further aspect of the invention, it is to be noted that the uses for this device are not limited to treatment of carpal tunnel disorder.

It is evident that self-application of traction to the upper extremity may be desirable, appropriate, and beneficial in the treatment of maladies including sports injuries, work related injuries, stress and fatigue related disorders, mobility and motion disorders, muscle and neurological afflictions, stroke, and post-surgical applications involving the upper extremity which may comprise the wrist, forearm, upper arm, elbow or shoulder.

The invention may also be applied to provide traction to a lower extremity as well as the neck.

FIG. 9 illustrates a method of the present invention whereby the tensioning cable 120 passes through a receptacle 121 which may be an eyelet 121 affixed to a stationary object 150, which may be a wall or door molding 150. The user 50, seated in an upright position 62 pulls the handle 140 on the distal end of the tensioning cable 150 away from the stationary object 150 causing tension on the foot retaining device 198 thereby causing traction to the lower extremity. The user releases the traction whereupon the process is repeated.

FIG. 10 is an illustration of still another method of the present invention whereby tensioning cable 120 passes through receptacle 198 affixed to a stationary object 150 which can be a wall, door molding, heavy furniture, or the like, and is attached to the head retraining device 160. The user 50, holding handle member 140 at the distal end of tensioning cable 120 pulls the tensioning cable 120 through the receptacle 198 causing tension on the head retaining device 160 thereby causes traction to the neck. User releases the tension whereupon the process is repeated.

Figure 11:
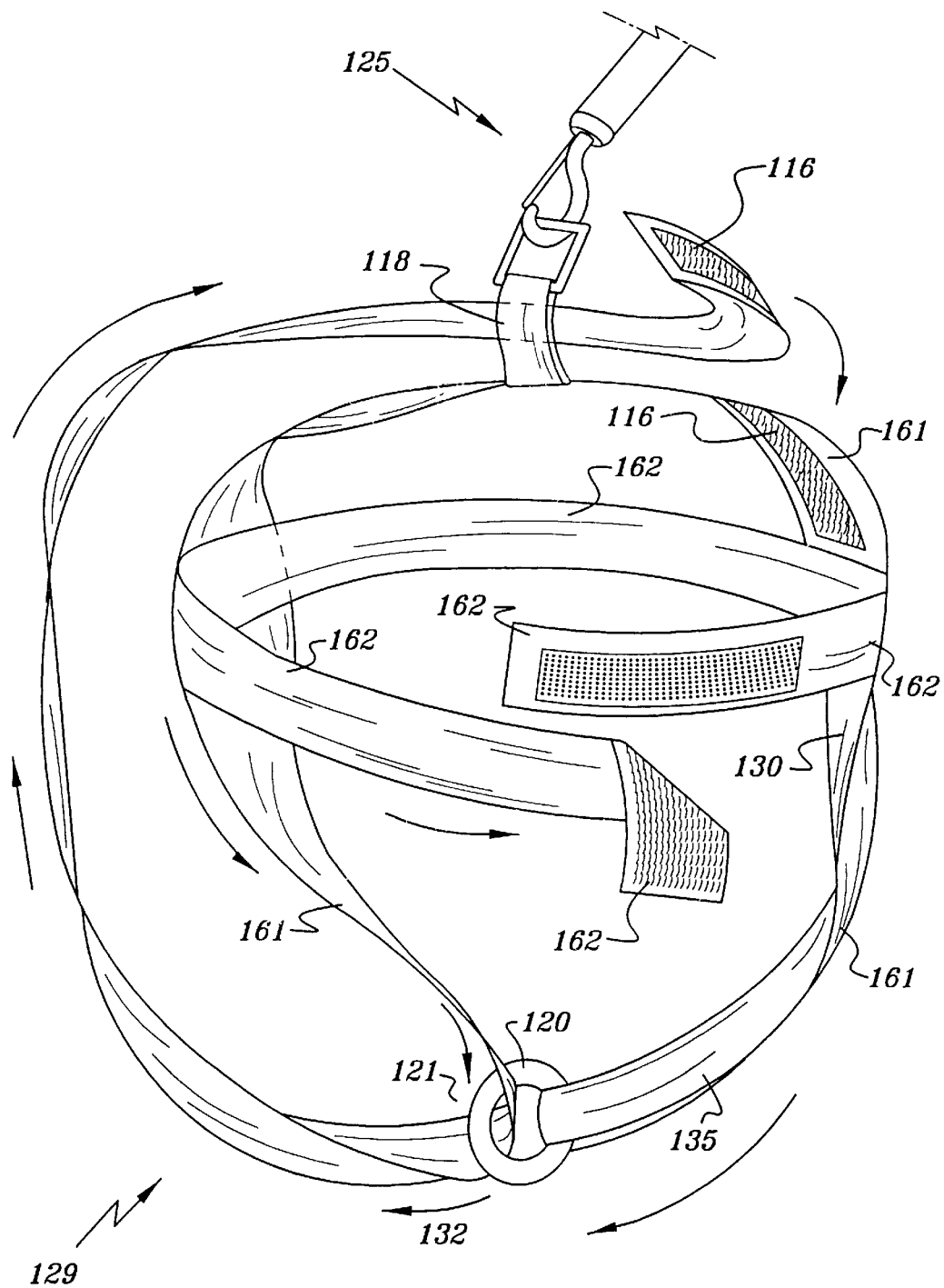
FIG. 11 shows a perspective view of the head-retaining device attached to the tensioning cable.

FIG. 11 is a detail view of the adjustable head-retaining device comprising a one or two piece upper band 161 which traverses the top of the head, a two-piece forehead band 162 which traverses the circumference of the head and fastens at the forehead 61, and two lower chin restraining bands 135. The device can be constructed of a woven nylon band 130 or similar material with hook and loop fasteners 125. Referring again to FIG. 11, the device further comprises a strap or straps 130 for affixing to the tensioning cable 120. As further illustrated in the preferred embodiment, chin band 135 comprises a retaining loop 122 through which passes the second chin retaining band 135, whereupon it is pulled upward to the top of the head and fastens 116 to the top band.

The manufacturing, assembly and use of this invention is very simple. Nonetheless the inventor suggests the following procedure for the consumer market.

1. Connect an interface connecting member to a wrist of the Do-It-Yourself patient on one end and to an anchor on the other end.

2. Connect one end of tension cable to said interface connecting member.

3. Connect the distal end of said tension cable to an anchor.

4. Use as a normal traction device.

The shape and size and quantity of the various members and components may be modified. The color, aesthetics and materials may be enhanced or varied. A different method of anchoring may be employed. Additional complimentary and complementary functions and features may be added. A more economical version of the device may be adapted. A different means may be used to don the interface onto the wrist of do-it-yourself patient.

Accordingly, while only a few embodiments of the present invention have been shown and described, it is obvious that many changes and modifications may be made thereunto without departing from the spirit and scope of the invention.

What is claimed is:

1. A traction device for prevention and relief of carpal tunnel syndrome of a human limb comprising:

an adjustable wrist retaining device shaped to wrap around a wrist of the user;

a looped tensioning cable having two ends and coupled to said adjustable wrist retaining device; and at least two releasable fasteners that couple said ends of said looped tensioning cable to said adjustable wrist retaining device;

wherein said adjustable wrist retaining device is secured over said wrist of the user and said looped tensioning cable is looped around a stable anchor, and wherein the user pulls away from said stable anchor stretching said looped tensioning cable and applying traction to said wrist of the user.

2. The traction device of claim 1, wherein said looped tensioning cable is looped around another human limb.

3. The traction device of claim 1, wherein said looped tensioning cable is looped around an external anchor.

4. The traction device of claim 1, wherein said adjustable wrist retaining device is U-shaped to easily wrap around said wrist.

5. The traction device as claimed in claim 1, wherein said at least two releasable fasteners comprise a hook and a loop.

6. A process for prevention and relief of carpal tunnel syndrome of a human limb comprising the steps of:
- wrapping an adjustable wrist retaining device around a wrist of the user;
- connecting a looped tensioning cable to an anchor; and
- attaching releasable fasteners between said adjustable wrist retaining device and said looped tensioning cable.

7. The process for prevention and relief of carpal tunnel syndrome of claim 6, wherein said step of connecting a looped tensioning cable comprises connecting said looped tensioning cable to another human limb.

8. The process for prevention and relief of carpal tunnel syndrome of claim 6, wherein said step of attaching releasable fasteners comprises connecting a loop and a hook.

9. An apparatus for applying extremity traction comprising:
- a looped tensioning cable having two ends;
- a gloved device coupled to said looped tensioning cable; and
- at least two releasable fasteners that couple said ends of said looped tensioning cable to said gloved device;

wherein said gloved device is secured over the hand of the user and said looped tensioning cable is looped over a stable anchor, and wherein the user pulls away from said stable anchor stretching said looped tensioning cable and applying traction to said wrist of the user.

10. The apparatus as claimed in claim 9, wherein said looped tensioning cable is made of material selected from the group consisting of bungie cords, rubber, elastic, non-elastic, rope, metal spring and string.

11. The apparatus as claimed in claim 9, wherein said at least two releasable fasteners comprise a hook and a loop.

12. The method as claimed in claim 11, wherein said step of causing tension in said tensioning cable comprises forming a loop in said tensioning cable and attaching both ends of said tensioning cable to the extremity retaining device through releasable fasteners.

13. The method of using an apparatus for applying extremity traction comprising the following steps:
- affixing a looped tensioning cable to a fixed object;
- causing tension in the tensioning cable at the extremity by pulling the extremity away from the fixed object;
- moving the extremity toward the fixed object releasing tension at the extremity; and
- repeating moving away from and moving toward the fixed object one or more times.

* * * * *